(12) United States Patent
Mukhopadhyay et al.

(10) Patent No.: US 7,396,965 B2
(45) Date of Patent: Jul. 8, 2008

(54) METHOD FOR PRODUCING FLUORINATED ORGANIC COMPOUNDS

(75) Inventors: Sudip Mukhopadhyay, Buffalo, NY (US); HsuehSung Tung, Getzville, NY (US); Haridasan Nair, Williamsville, NY (US); Jingji Ma, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 226 days.

(21) Appl. No.: 11/127,892

(22) Filed: May 12, 2005

(65) Prior Publication Data

US 2006/0258891 A1    Nov. 16, 2006

(51) Int. Cl.
*C07C 21/18* (2006.01)
(52) U.S. Cl. .................. 570/172; 570/155; 570/156
(58) Field of Classification Search .......... 570/172, 570/155, 156
See application file for complete search history.

(56) References Cited

U.S. PATENT DOCUMENTS

| 2,462,402 A | 2/1949 | Joyce, Jr. ................ 260/653 |
| 5,157,171 A | 10/1992 | Sievert et al. ............... 570/151 |
| 5,162,594 A | 11/1992 | Krespan ..................... 570/126 |
| 5,227,547 A | 7/1993 | Ohnishi et al. ............. 570/172 |
| 5,326,913 A | 7/1994 | Aoyama et al. ............ 570/172 |
| 5,416,246 A | 5/1995 | Krespan et al. ............ 570/151 |
| 5,929,293 A | 7/1999 | Krespan et al. ............ 570/153 |
| 6,184,426 B1 | 2/2001 | Belen'Kill et al. ......... 570/172 |

FOREIGN PATENT DOCUMENTS

| WO | WO 97/02227 | 1/1997 |
| WO | WO 98/42645 | 10/1998 |

OTHER PUBLICATIONS

R. Eric Banks, Michael G. Barlow, Mahmood Nickkho-Amiry, *Journal of Fluorine Chemistry* 82 (1997) 171-174.
Belen'Kii GG et al: "Electrophilic, catalytic alkylation of polyfluoroolefins by some fluoroalkanes" vol. 108, No. 1, Mar. 1, 2001 p. 15-20 XP004231215.

*Primary Examiner*—Elvis O Price
(74) *Attorney, Agent, or Firm*—Colleen D. Szuch

(57) ABSTRACT

A method for preparing fluorinated organic compounds wherein at least one fluorinated olefin is reacted with methyl fluoride in the gas-phase and in the presence of a Lewis Acid catalyst to form at least one product having at least 3 carbon atoms.

4 Claims, No Drawings

METHOD FOR PRODUCING FLUORINATED ORGANIC COMPOUNDS

BACKGROUND OF INVENTION (1) Field of Invention:

This invention relates to novel methods for preparing fluorinated organic compounds via a gas-phase reaction. In particular, the present invention relates to methods of producing fluorinated alkanes, fluorinated alkenes, and fluorocarbon polymers via a gas-phase reaction.

(2) Description of Related Art:

Hydrofluorocarbons (HFC's), in particular hydrofluoroalkenes such as 2,3,3,3-tetrafluoro-1-propene (R-1234yf) and hydrofluoroalkanes such as 1,1,1,2,2-pentafluoropropane (R-245cb), are known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 6,184,426 (Belen'Kill) describes a method of making R-245cb via the liquid phase reaction of tetrafluoroethylene (TFE) and methyl fluoride in the presence of antimony pentafluoride catalyst. Other processes for producing hydrofluoroalkanes include those described in WO 97/02227 (DuPont) wherein carbon tetrafluoride or chloro-trifluoromethane are reacted with a fluorinated ethylene compound in the liquid phase to produce a fluorinated propane or a chlorofluorinated propane.

Methods of prepareing hydrofluoroalkenes are likewise known. For example, the preparation of R-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

However, the above-mentioned processes have a serious disadvantage in that they are solvation reactions; that is, a solvent is necessary to facilitate the reaction. Solvation reactions have a number of disadvantages. For example, certain solvents pose health risks and the risk of environmental contamination. Also, their use can dramatically increase the costs associated with synthesizing hydrofluorocarbons due to the cost of the solvent itself as well as the added expense of recovering the solvent. An additional disadvantage is the fact that the product is produced in the liquid phase instead of the gas phase. Liquid phase separation processes are substantially more difficult and costly compared to gas phase separations.

Therefore, there remains a need for methods of efficiently preparing certain hydrofluorocarbons, such as R-1234yf and R-245cb, via a gas-phase reaction. These and other needs are satisfied by the present invention.

SUMMARY OF THE INVENTION

Applicants have discovered an economical method for producing fluorinated organic compounds, including hydrofluoroproanes and hydrofluoropropenes, involving the reaction of a fluorinated olefin with methyl fluoride in the gas phase. Conventionally, solvation agents are used to produce hydrofluoroproanes. It was generally believed that these solvation agents, which could bring the reactants into physical contact, were necessary in order to facilitate a synthesis reaction. The use of solvating agents required that these reactions be conducted in the liquid phase. Applicants have discovered, however, that a synthesis reaction can also occur in the absence of solvation agents and therefore can be conducted in the gas phase. In addition, Applicants have also discovered that such a gas phase process produces not only a hydrofluoroproane product, but also a hydrofluoropropene coproduct.

Thus, according to certain preferred embodiments of the present invention, processes are provided for preparing fluorinated organic compounds by reacting, in the gas-phase and in the presence of a Lewis Acid catalyst, methyl fluoride with at least one fluorinated olefin having the structure:

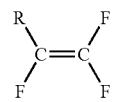

wherein R is F, Cl, $C_1$-$C_2$ fluorinated alkyl, or a two-carbon fluorinated alkenyl to produce at least one product having at least 3-carbons. Preferably, this reaction is conducted essentially free of solvation agents.

Without being bound to any particular theory, it is believed that according to certain preferred embodiments, the methyl fluoride interacts with the catalyst to form a carbonium ion. This carbonium ion, in turn, reacts with the fluorinated olefin to form a halogenated alkane. Additionally, a portion of the halogenated alkane can continue to react with the catalyst to form a halogenated alkene. Thus, synthesis methods according to the present invention have the distinctive advantage of not requiring a solvation agent and, because the product is synthesized in the gas-phase, product separation and purification is economical.

In particularly preferred embodiments, methyl fluoride is reacted with tetrafluoroethylene, chlorotrifluoroethylene, or some mixture thereof in the presence of activated carbon catalyst impregnated with an antimony pentafluoride to produce R-1234yf, R-245cb, or some combination thereof.

DETAILED DESCRIPTION OF THE PREFERRED EMBODIMENTS

The present invention provides a gas-phase, catalytic addition reaction wherein at least one fluorinated olefin is combined with methyl fluoride to produce a product having at least 3 carbon atoms. According to certain preferred embodiments, the reaction can be represented as:

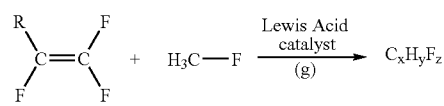

wherein R is F, Cl, $C_1$-$C_2$ fluorinated alkyl, or a two-carbon fluorinated alkenyl, x is an integer from 3 to 5, y is an integer from 2 to 3, and z is an integer from 4 to 9.

As used herein, the term "fluorinated" refers to an organic compound having at least one fluorine atom. Thus, fluorinated compounds include hydrofluorocarbons, fluorocarbons, chlorofluorocarbons, and the like.

Preferred fluorinated olefin reactants include $CClF=CF_2$, $CF_2=CF_2$, $CF_3CF=CF_2$, $CF_3CF_2CF=CF_2$, and $CF_2=CF-CF=CF_2$, with tetrafluroethylene (TFE) and chlorotrifluoroethylene (CTFE) being particularly preferred. Each of these compounds are readily available from a variety of commercial sources. In certain preferred embodiments, the fluorinated olefin reactant will comprise a combination of at least two of the above-mentioned fluorinated olefins.

A Lewis Acid catalyst according to the present invention is a metallic or metalloid halide that is capable of accepting a pair of electrons from a coordinate covalent bond. Such catalysts include, but are not limited to, compounds containing at least one atom selected from the group consisting of Sb and Al, and at least one atom selected from the group consisting of F, Cl, Br, and I. Examples of chloride catalysts suitable for use in the present invention include, but are not limited to, $SbCl_5$ and $AlCl_3$, and partially fluorinated compounds of such chlorides. Examples of fluoride catalysts suitable for use in the present invention include, but are not limited to, $SbF_5$, $SbF_3$, and partially chlorinated compounds of such fluorides. Preferred Lewis Acid catalysts include $SbF_5$, $SbF_3$, and $SbCl_5$, with $SbF_5$ being particularly preferred. In certain preferred embodiments, combination of at least two of the above-mentioned catalysts may be used together.

In certain preferred embodiments, the Lewis Acid catalysts are impregnated onto an activated carbon substrate. Impregnated activated carbons according to the present invention are carbonaceous materials which have catalytic compounds finely distributed on their internal surface. Activated carbon materials generally have a porous structure and a large internal surface area. The volume of pores of the activated carbons is generally greater than 0.2 ml/g and the internal surface area is generally greater than 400 m²/g. The width of the pores ranges from 0.3 nm to several thousand nm.

Impregnation utilizes the physical properties of activated carbon to increase the activity of the catalyst. For example, the activated carbon, in part, is used as an inert porous carrier material for distributing catalysts on the material's large internal surface, thus making them more accessible to the reactants.

In certain preferred embodiments, the impregnation occurs by depositing the catalyst on dried activated carbon under a nitrogen blanket at 0-5° C.

Hydrofluorocarbon products of the present invention preferably are of the formula:

wherein x is an integer from 3 to 5,
y is an integer from 2 to 3, and
z is an integer from 4 to 9.

Preferred hydrofluorocarbon products produced by the present invention include fluorinated alkanes and fluorinated alkenes. Where the present invention is practiced as a continuous process, the product stream will include either or both of these products. Preferred fluorocarbon products will have at least 3 carbon atoms and may, for embodiments in which R is a fluorinated alkenyl, be a polymer. Examples of preferred hydrofluorocarbon products include, but are not limited to, $CH_3CF_2CF_3$, $CH_3CF_2CF_3$, $CH_3CF_2CF_2CF_3$, $CH_3CF_2CF_2CF_2CF_3$, $CH_2=CFCF_3$, $CH_2=CFCF_2CF_3$, and $CH_2=CFCF_2CF_2CF_3$. Highly preferred hydrofluorocarbon products include tetrafluoropropenes, particularly 2,3,3,3-tetrafluoro-1-propene, and pentafluoropropanes, particularly 1,1,1,2,2-pentafluoropropane.

In a highly preferred embodiment of the present invention, methyl fluoride is reacted with chlorotrifluoroethylene in the gas-phase and in the presence of catalyst comprising activated carbon impregnated with antimony pentafluoride. One would expect that the major product of such a reaction to be 1-chloro-2,2,3,3-tetrafluoropropane. Surprisingly, Applicants have found that the actual product of this reaction is primarily a mixture of 2,3,3,3-tetrafluoro-1-propene and 1,1,1,2,2-pentafluoropropane. Although not being bound by any particular theory, Applicants believe that this embodiment proceeds according to the reaction scheme:

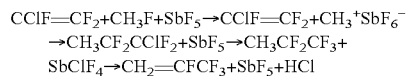

The reactions of the present invention are conducted in the gas-phase, preferably at a temperature of from about 40° C. to about 150° C. and at a pressure of from about 0.5 psig to about 150 psig. More preferably, reactions are conducted at from about 50° C. to about 70° C. and at a pressure from about 10 psig to about 20 psig.

The optimal temperature and pressure for a particular reaction will depend, in part, on the final product desired. Although, the conversion of the reactants generally increases with an increase in temperature and pressure, the relatively high vapor pressure of $SbF_5$ moderates the reaction temperature and pressure. One skilled in the art would, based on the present disclosure, be able to readily determine the optimum temperature and pressure for a given reaction without having to conduct undue experimentation.

The present invention can be conducted via a batch or, more preferably, a continuous process. In certain preferred embodiments utilizing a continuous process, the reactants are mixed together, heated, then passed through a catalyst bed to produce a product stream. Preferably, the desired product yields are obtained with a single pass of the reactant mixture through the catalyst bed. However, the present invention is not limited to such operations but may include operations having multiple passes. In certain preferred embodiments, acids in the product stream are neutralized by a scrubber. The product stream can be fractionated (for example, by distillation) to isolate the individual products.

EXAMPLES

Additional features of the present invention are provided in the following examples, which should not be construed as limiting the claims in any way.

Examples 1-5

These examples show the activity of different catalysts.

Catalyst Preparation:

Catalyst A

A catalyst comprising activated carbon impregnated with $SbF_5$ is prepared by first drying 100 g of activated carbon in a oven at 180° C. under vacuum for 72 hours. After drying, the carbon is covered with aluminum foil and then cooled gradually to room temperature under vacuum.

A 250 ml HDPE bottle is flushed with anhydrous $N_2$ to remove ambient air. Approximately 50 g of the dried activated carbon is then placed in the bottle inside a glove box under a $N_2$ blanket. Inside the glove box, 50 g of $SbF_5$ is slowly added (approximately 2 g/min) to the activated carbon while swirling the contents of the bottle. The contents of the bottle are stirred with a plastic rod until all the liquid is adsorbed into the pores of carbon or until fumes of $SbF_5$ are no longer emitted.

Catalyst B

This procedure is the same as that described for catalyst A, except that (1) the bottle was emerged in a 0-5° C. temperature bath to facilitate the adsorption of $SbF_5$ through the pores of activated carbon; and (2) the $SbF_5$ is added to the bottle at a rate of 5 g/min.

Catalyst C

This procedure is the same as that described for catalyst B, except that only 20 g of $SbF_5$ is added to the 50 g of activated carbon Catalyst D This procedure is the same as that described for catalyst B, except that the 50 g of activated carbon is impregnated with 30 g of $SbCl_5$ and is then fluorinated in a ½ inch Monel reactor with 30 g/hr of HF at 70° C. over a period of 20 hours under 50 psig pressure. After the fluorination, 50 Standard Cubic Centimeters per Minute (SCCM) of $N_2$ is passed through the catalyst bed at 30° C. for 30 hours to remove free HF from the bed.

Catalyst E

This procedure is the same as that described for catalyst B, except that the 50 g of the dried activated carbon is impregnated with 50 g of $SbF_3$ and is then fluorinated in a ½ inch monel reactor with 10 g/hr of $F_2$ (a mixture of 50 wt % $N_2$ and 50 wt % $F_2$) at 70° C. over a period of 30 hours under 50 psig pressure. After the fluorination, 50 SCCM of 100 wt % $N_2$ is passed through the bed at 30° C. for 2 hours to remove free $F_2$ from the bed.

Catalyst Activity:

The activity of each of the above-mentioned catalysts are shown by the following procedure.

A ½-inch Monel flow reactor is charged with 50 g of a freshly prepared catalyst and then uniformly heated to 50° C. A gaseous mixture of CTFE and $CH_3F$ at 20 psig is heated to 40° C. in a pre-heater that is connected to the reactor. The heated reactant mixture is passed into the reactor at a flow of 20 SCCM. The exit line from the reactor is connected to an on-line GC and GCMS for analysis. A 15% KOH scrubber solution was used at 50° C. to neutralize acids coming out from the reactor. The gas stream coming out of the scrubber solution is then condensed in a cylinder under liquid $N_2$ and then finally fractionated (distilled) to isolate products. The results for each catalyst are shown below:

| Example | Catalyst | % Conv. of CTFE | % Conv. to $CF_3CF=CH_2$ | % Conv. to $CF_3CF_2CH_3$ |
|---|---|---|---|---|
| 1 | A | 15 | 52 | 34 |
| 2 | B | 22 | 54 | 37 |
| 3 | C | 20 | 53 | 37 |
| 4 | D | 2 | 2 | 6 |
| 5 | E | 12 | 27 | 39 |

It is observed that Catalyst B is the most active catalyst under the reaction conditions shown.

Examples 6-14

These examples show the conversion rates of chlorotrifluoroethylene (CTFE) and tetrafluoroethylene (TFE) in the presence of a Sb-based catalyst.

A ½-inch Monel flow reactor is charged with 50 g of a freshly prepared catalyst B and then uniformly heated to the temperature indicated in the table below. A gaseous mixture of CTFE or TFE and $CH_3F$ is heated to 10° C. below the reactor temperature. The heated reactant mixture is then passed into the reactor at a flow of 20 SCCM at the pressure indicated in the table below. The exit line from the reactor is connected to an on-line GC and GCMS for analysis. A 15% KOH scrubber solution was used at 50° C. to neutralize acids coming out from the reactor. The gas stream coming out of the scrubber solution is then condensed in a cylinder under liquid $N_2$ and then finally fractionated (distilled) to isolate products. The results for each experimental run are shown below:

| Experiment No. | T (° C.) | P (psig) | Olefin Reactant | % Conv. of CTFE/TFE | % Conv. to $CF_3CF=CH_2$ | % Conv. to $CF_3CF_2CH_3$ |
|---|---|---|---|---|---|---|
| 6 | 50 | 1.2 | CTFE | 15 | 48 | 45 |
| 7 | 50 | 5 | CTFE | 17 | 52 | 40 |
| 8 | 50 | 20 | CTFE | 22 | 54 | 37 |
| 9 | 60 | 2.1 | CTFE | 24 | 50 | 40 |
| 10 | 70 | 3.5 | CTFE | 21 | 42 | 42 |
| 11 | 50 | 3.2 | TFE | 35 | 20 | 74 |
| 12 | 60 | 3.2 | TFE | 37 | 22 | 72 |
| 13 | 60 | 20 | TFE | 38 | 26 | 68 |
| 14 | 50 | 100 | TFE | 39 | 18 | 64 |

It is observed that the reaction is generally more selective for TFE compared to CTFE, but that a CTFE feed produces a higher percent conversion to $CF_3CF\!=\!CH_2$.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising reacting methyl fluoride with at least one fluorinated olefin having the structure:

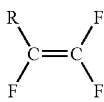

wherein R is F, Cl, $C_1$-$C_2$ fluorinated alkyl, or two-carbon fluorinated alkenyl, to produce at least one product having at least 3 carbon atoms, wherein said reaction occurs in the gas-phase and in the presence of a Lewis Acid catalyst, wherein said product includes a fluorocarbon polymer.

2. A method of preparing fluorinated organic compounds comprising reacting methyl fluoride with at least one fluorinated olefin having the structure:

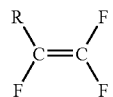

wherein R is F, Cl, $C_1$-$C_2$ fluorinated alkyl, or two-carbon fluorinated alkenyl, to produce at least one product having at least 3 carbon atoms, wherein said reaction occurs in the gas-phase and in the presence of a Lewis Acid catalyst, wherein said product includes 2,3,3,3-tetrafluoro-1-propene.

3. A method of preparing fluorinated organic compounds comprising reacting methyl fluoride with at least one fluorinated olefin having the structure

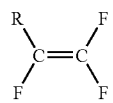

wherein R is F, Cl, $C_1$-$C_2$ fluorinated alkyl, or two-carbon fluorinated alkenyl, to produce at least one product having at least 3 carbon atoms, wherein said reaction occurs in the gas-phase and in the presence of a Lewis Acid catalyst, wherein said Lewis Acid catalyst is impregnated on activated carbon.

4. The method of claim 3 wherein said activated carbon is essentially anhydrous.

* * * * *